United States Patent [19]
Davenport et al.

[11] Patent Number: 4,593,125

[45] Date of Patent: Jun. 3, 1986

[54] ACYLATION OF NAPHTHALENES

[75] Inventors: Kenneth G. Davenport; H. Clay Linstid, III, both of Corpus Christi, Tex.

[73] Assignee: Celanese Corporation, New York, N.Y.

[21] Appl. No.: 711,344

[22] Filed: Mar. 13, 1985

[51] Int. Cl.[4] ............................................. C07C 45/46
[52] U.S. Cl. ...................................... 568/319; 568/42; 568/322; 568/323
[58] Field of Search .................. 568/319, 322, 323, 42

[56] References Cited

U.S. PATENT DOCUMENTS

| | | | |
|---|---|---|---|
| 4,061,779 | 12/1977 | Lake et al. | 568/323 |
| 4,082,807 | 4/1978 | Eiglmeier | 568/316 |
| 4,474,990 | 10/1984 | Jansons | 568/319 |

FOREIGN PATENT DOCUMENTS

| | | | |
|---|---|---|---|
| 2653601 | 11/1976 | Fed. Rep. of Germany | 568/319 |
| 54-135756 | 10/1979 | Japan | 568/319 |

OTHER PUBLICATIONS

Akhmedova et al., Chem. Abst., vol. 98, #198772t (1983).
Cavrini et al., Chem. Abst., vol. 97, #38629c (1982).

*Primary Examiner*—James H. Reamer
*Attorney, Agent, or Firm*—D. R. Cassady; M. Turken

[57] ABSTRACT

Naphthalene substituted in the 2- or β-position with an electron-donating substituent can be acylated with high regioselectivity in the 6-position by using an acylating agent in substantially anhydrous hydrogen fluoride which functions both as catalyst and solvent.

10 Claims, No Drawings

ACYLATION OF NAPHTHALENES

BACKGROUND OF THE INVENTION

Many general comments are made in the patent and technical literature that the Friedel-Crafts type acylation of β-substituted naphthalenes can be carried out in the presence of any Friedel-Crafts catalyst. This statement is then substantiated by particular reference to experiments using, e.g., aluminum chloride or zinc chloride catalyst in nitrobenzene or chlorinated hydrocarbons, or boron trifluoride optimally in the presence of hydrogen fluoride.

Typically these references do not identify the position of the acyl substitution on the naphthalene ring or do not provide such substitution in the 6-position with sufficient regioselectivity that a large scale manufacturing program can be developed using the disclosed technology.

In our work on developing precursors for aromatic monomers for polyesters, pharmaceuticals, and other value-added chemicals, we were interested in obtaining nearly exclusively 6-acyl-2-naphthol and related 6-acyl-2-substituted naphthalenes in high conversions with high regioselectivity.

A search of the literature provided the following pertinent prior art.

Japanese Kokai Sho No. 54 [1979]-135756, Yasui et al., describes the preparation of 2-alkyl-6-acylnaphthalene from the 2-alkylnaphthalene and acyl fluoride in hydrogen fluoride with boron trifluoride as a catalyst and in boron trifluoride as a catalyst-solvent. The reaction is claimed to be carried out at between −50° C. and +100° C.; however, a reading of the textual portion of the disclosure teaches that yields and 6,-2-selectivity decrease markedly outside the range of about −10° to +10° C.

Eiglmeier, in U.S. 4,082,807, teaches the acylation of 2-methoxynaphthalene in anhydrous hydrogen fluoride with diketene to yield 1-acetoacetyl-2-methoxynaphthalene in 88% yield at −25° C. to −35° C.

Additional literature which teaches the Friedel-Crafts acylation of naphthalene and its β-substituted derivatives include:

Alvarez in U.S. Pat. No. 3,758,544, and U.S. Pat. No. 3,873,594, teaches that in conventional inert solvents, i.e., chlorinated hydrocarbons, Friedel-Crafts acylation of 2-methoxynaphthalene with acetyl chloride is accomplished in only low yields. He found that chlorination in the 1-position was necessary to improve the yield of the corresponding 6-acetyl derivative. In the cited patent, anhydrous hydrogen fluoride is identified as a typical but not preferred Friedel-Crafts catalyst.

Muessdoerffer and Niederprum in German Offenlegungschrift No. 2,616,986, published Oct. 27, 1977, claimed the acylation of phenols and substituted phenols with an acyl chloride in the presence of hydrogen fluoride to yield the 4-acyl derivative in high yield with high selectivity. The inventors disclose that 2-naphthol and 7-chloro-2-naphthol can be acylated according to their invention. They do not teach a method for the acylation of the naphthol derivatives nor do they indicate what isomer or isomers are manufactured by the claimed process. In view of the other cited prior art, one might be presumed to forecast that the 1-acyl-2-hydroxynaphthalene would be formed.

Lodewijk, U.S. Pat. No. 3,803,245, discloses the acylation of 2-methoxynaphthalene using aluminum chloride catalyst in nitrobenzene with aluminum chloride, zinc chloride, or similar Friedel-Crafts catalysts.

*Organic Synthesis*, Vol. 53, p.5, teaches the acylation of 2-methoxynaphthalene in nitrobenzene with acetyl chloride in 45-48% yield.

Further references teaching the acylation of naphthalene in Friedel-Crafts type reactions include:

| | |
|---|---|
| Kacer and Krause | U.S. Pat. No. 1,841,445 |
| Kranzlein et al. | U.S. Pat. No. 1,910,470 |
| Skraup | U.S. Pat. No. 1,995,402 |
| Skraup | U.S. Pat. No. 2,087,213 |
| Boese | U.S. Pat. No. 2,214,117 |
| Lieber | U.S. Pat. No. 2,287,110 |
| Mikeska and Lieber | U.S. Pat. No. 2,288,319 |
| Lieber | U.S. Pat. No. 2,307,891 |
| Lieber | U.S. Pat. No. 2,353,053 |
| Johnson and Graber | U.S. Pat. No. 2,683,738 |
| Alvarez | U.S. Pat. No. 3,637,767 |
| Giordano and Casagrande | U.S. Pat. No. 4,328,356 |

Given and Hammick, *Journal Chemical Society* (1947) 1237

Bui-Hoi et al., *Journal Organic Chem.*, 16,988–94 (1951)

Gupta and Haksar *Agra Univ. J. of Res.*, (Sci) XI, Pt. 2, 165–6 (1962)

Arai, *Tetrahedron Letters*, 24, #14, pp. 1531–34(1983)

Girdler et al., *Journal Chemical Society* [1966] C(Org.), 181

Harrison et al., *Journal Med. Chem.*, 13,203(1970) and the following Chemical Abstract references:

CA 50,5625 c
CA 50,7139 e
CA 56,14136 d
CA 57,15022 d
CA 58,6663 e
CA 67,10907 y
CA 74,16093 w
CA 80,2790 h

The process of this invention leads to intermediates in the manufacture of valuable pharmaceuticals as disclosed in the Alvarez patents, cited above. The process also provides intermediates for the manufacture of monomers as disclosed in the Yasui Japanes patent, loc cit.

Using the teaching of the above cited references, commercialization of the process has been difficult. Aluminum chloride, zinc chloride, and similar salts used as catalysts in their anhydrous state absorb water rapidly, hydrolyzing, and thus becoming useless in the reaction. Nitrobenzene and the polyhalogenated hydrocarbons utilized as solvents are high boiling, toxic materials.

Nitrohydrocarbons, in the presence of the water invariably required during the usual work-up, give rise to inseparable emulsions. Also, the usual Friedel-Crafts catalysts, when admixed with nitrohydrocarbons, generate a substantial exothermic reaction which can be difficult to control. Conversions are low. When using metal halides in nitrohydrocarbons, isomeric mixtures are common, causing additional separation steps to be necessary.

For all of the above reasons and others, we developed the herein claimed process.

SUMMARY OF THE INVENTION

This invention relates to an improved process for the acylation of naphthalene substituted in the 2-position by an electron-donating substituent. By the process of this invention the naphthalenic compound to be acylated is brought in contact with substantially anhydrous hydrogen flouride, contacted with an appropriate quantity of the acylating agent, and heated to from about 40° C. to about 100° C. for a time sufficient to cause substantially complete conversion of the naphthalene compound to an acyl naphthalene. The hydrogene fluoride is then removed by evaporation and the acylnaphthalene is isolated. Although the process of this invention is useful in acylating any appropriately substituted naphthalene, it is particularly useful in the acylation of compounds of the formula:

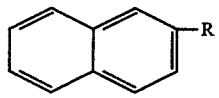

wherein R is hydroxy, lower alkyl, lower alkoxy, lower alkylthio, and halo.

The acylating agent useful in the process of the present invention may conveniently be any commercially useful acylating agent. The reaction is more particularly useful when carried out with the lower alkyl carboxylic acids, acid anhydrides, acid halides and ketene.

DETAILED DESCRIPTION OF THE INVENTION

The purpose of the present invention is to (1) increase the conversion of an appropriately β-substituted naphthalene to an acylnaphthalene; (2) increase the amount of 6-acyl substitution compound in the produced (3) lower the amount of by-products, particularly tarry by-products in the acylated material; (4) simplify the manipulative steps needed to obtain the desired product; and (5) thereby lower the cost of manufacture of the product. Other advantages to be realized by practicing the process of the present invention will become obvious to those skilled in the art by studying the following description and the preferred embodiments of the invention.

The compounds useful in the process of this invention are the 2-substituted naphthalenes wherein the substituent is traditionally known as an ortho-para directing group, an electron-donating group, or by similar designation. Further, the substituent must not be reactive with hydrogen fluoride, as for example to irreversibly form a hydrofluoride salt, thus defeating the ortho-para directing influence of the group.

Typically, the compounds most useful in the process of this invention are characterized by the formula:

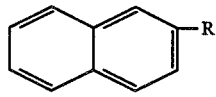

wherein R is a member of the group consisting of hydroxy, lower alkyl, lower alkoxy, lower alkylthio, and halo.

As used in the context of this invention: Lower alkyl means $C_1$ to $C_4$ alkyl and includes the methyl, ethyl, n-propyl, iso-propyl, n-butyl, sec-butyl, iso-butyl, and tert-butyl moieties.

Lower alkoxy is meant to be a member of the group consisting of methoxy, ethoxy, n-propoxy, iso-propoxy, n-butoxy, sec-butoxy, iso-butoxy, and tert-butoxy.

Lower alkylthio is methylthio, ethylthio, n-propylthio, iso-propylthio, n-butylthio, sec-butylthio, iso-butylthio, or tert-butylthio.

Halo includes fluoro, chloro, bromo, and iodo. Compounds particularly useful in the process of the invention include:
2-naphthol
2-methylnaphthalene
2-ethylnaphthalene
2-isopropylnaphthalene
2'-(sec-butyl)naphthalene
2-methoxynaphthalene
2-ethoxynaphthalene
2-n-propoxynaphthalene
2-(tert-butoxy)naphthalene
2-methylthionaphthalene
2-ethylthionaphthalene
2-isopropylthionaphthalene
2-fluoronaphthalene
2-chloronaphthalene
2-bromonaphthalene
2-iodonaphthalene, and the like.

The acylating agent most particularly useful for the present invention process includes a lower alkyl carboxylic acid or a derivative of a lower alkyl carboxylic acid, as for example a carboxylic acid halide or anhydride, wherein by lower alkyl is meant the $C_2$-$C_4$ carboxylic acids and derivatives thereof.

Examples of acylating agents particularly useful in the present invention include acetic acid, propionic acid, butyric acid, isobutyric acid, acetic anhydride, propionic anhydride, acetyl chloride, propionyl chloride, acetyl fluoride, propionyl fluoride, butyryl fluoride, acetyl iodide, propionyl bromide, and the like.

The process of the invention can be operated in a batch or semi-continuous manner. The acylating step of the process should be run in a closed system since hydrogen fluoride is a toxic material which has a high vapor pressure, boiling at about ambient room temperature, and the acylation step is carried out normally at above ambient room temperature, as for example at about 60° C. to about 80° C.

The process of the present invention is normally carried out in the following manner. The appropriately substituted naphthalene is brought into contact with substantially anhydrous hydrogen fluoride. Although an excess of hydrogen fluoride is acceptable and does not cause an appreciable loss of yield or regioselectivity, we have found it most advantageous to use about a 1:25 to about 1:50 mole ratio of naphthalene derivative to hydrogen fluoride.

The reaction can be carried out in the absence of an additional solvent. However, it is not detrimental to the reaction to use an additional inert solvent. Typically such additional solvents may include a chlorinated hydrocarbon or the like.

The mixture is cooled to at least about −30° C. preferentially by contacting the vessel containing the mixture with a cryogenic mixture of liquified gases, solid carbon dioxide or a similar material. The acylating agent is added and the reaction vessel sealed in a manner to withstand the vapor pressure of the hydrogen fluoride at the reaction temperature.

The cooling of the reaction vessel prior to addition of the acylating agent is only for the purpose of minimizing any reaction which might occur in admixing and to act to minimize any heat of dissolution of the reactants in hydrogen fluoride. The cooling step is merely manipulative and does not limit or define the reaction conditions.

Typically, then, the reaction vessel is heated to the temperature of reaction. In the process herein described and claimed, although some reaction does occur at temperatures below about 40° C., as for example at ambient room temperature, the greatest conversion to acylated naphthalene and the greatest regioselectivity to the 6-acyl isomer occurs between about 40° C. and about 100° C. In a preferred embodiment, the reaction occurs at a temperature range of from about 60° C. to about 80° C.

Reaction temperatures much above the above described range gives rise to products which are tarry, highly colored, and which are difficult to separate from the desired product by the usual isolation and purification techniques.

The reaction is allowed to occur at the temperature range until the formation of the acylnaphthalene is substantially complete, as for example, from about 30 to about 90 minutes.

In a preferred embodiment, a reaction time at the preferred temperature range of about 60 minutes gives rise to a high conversion of starting material to a product of which the acyl isomers contain a high proportion of the desired 6-acyl product without the co-manufacture of substantial quantities of undesired by-products.

The order of addition of the individual reactants and hydrogen fluoride as described above is only exemplitive. It is also to be considered to be within the scope of the invention to mix the β-substituted naphthalene and the acylating agent, cool to below the boiling point of hydrogen fluoride, and to then add the hydrogen fluoride and any inert solvent; adding the β-substituted naphthalene to a cooled solution of the acylating agent in hydrogen fluoride is also to be considered to be an equivalent method to carry out the adding or mixing step of the process of this invention.

The method or order of addition of the reactants does not change any of the other parameters or descriptions provided above.

After completion of the reaction, the vessel containing the reaction product is typically cooled to about the boiling point of the hydrogen fluoride, the vessel is vented and the hydrogen flouride is removed by evaporation and recovered. The residue is dissolved in an appropriate solvent, any remaining hydrogen flouride is neutralized and the resulting product isolated and purified in a manner well-known to those skilled in the art.

Typical of the process and the results therefrom are the following specific examples which are provided as a teaching of the process and are not to be construed as limiting thereupon.

EXAMPLE 1

A solution of 14.4 g. (0.1 moles) of β-naphthol and 24.0 g. (0.20 moles) of acetic acid is cooled to −30° C. in a stainless steel autoclave. The solution is purged with 50 psig nitrogen for 15 minutes. Hydrogen fluoride, 100 g. (5.0 moles), is added and the autoclave sealed.

The autoclave is rapidly heated to 80° C. and maintained at that temperature for 60 minutes. The autoclave is then rapidly cooled to 40° C. The hydrogen fluoride is purged from the autoclave at about 40° C. and then a nitrogen sweep is maintained for an additional one hour to remove the last distillable traces of hydrogen fluoride. The product is dissolved in ethyl acetate, poured onto ice, neutralized with an aqueous solution containing 45% potassium hydroxide until the aqueous solution was about pH 6.5. The aqueous layer is re-extracted with ethyl acetate. The organic layers are combined, washed with a saturated aqueous sodium chloride solution, dried and the solvent is removed in vacuo.

Conversion, 93%; selectivity to 6-hydroxy-2-acetonaphthane and its acetate, 76%.

In a similar manner, the following compounds are converted to the 6-acetyl derivative:
2-methoxynaphthalene to 6-methoxy-2-acetonaphthone
2-methylnaphthalene to 6-methyl-2-acetonaphthone

EXAMPLE 2

A solution of 14.4 g. (0.1 moles) of β-naphthol and 100 g. (5.0 moles) of hydrogen fluoride is prepared at −30° C. Acetic anhydride, 10.2 g. (0.10 moles) is added and the reaction autoclave is sealed. The autoclave is heated rapidly to 80° C. and held at that temperature for one hour. Isolation and purification of the resulting 6-hydroxy-2-acetonaphthone and its acetate is carried out as in Example 1. Conversion, 98%; selectivity to the 6,2 compound 63%. If the reaction is carried out with 0.2 moles of acetic anhydride the conversion is 99% and the selectivity is greater than 85%.

In a similar manner, the following compounds are converted to their 6-acyl derivative:
2-methoxynaphthalene to 6-methoxy-2-acetonaphthone
2-ethoxynaphthalene to 6-ethoxy-2-acetonaphthone
2-methylnaphthalene to 6-methyl-2-acetonaphthone
2-chloronaphthalene to 6-chloro-2-acetonaphthone

EXAMPLE 3

Acetyl fluoride, 9.3 g. (0.15 moles), is admixed with 100 g. (5.0 moles) of hydrogen fluoride at −30° C.; the mixture is then added to 14.6 g. (0.1 moles) of 2-fluoronaphthalene in a stainless steel autoclave. The autoclave is sealed and the temperature quickly raised to 75° C. In the manner of the first two examples of 6-acetyl-2-fluoronaphthalene is recovered.

EXAMPLE 4

Ketene (8.4 g., 0.2 moles generated by thermolysis of acetone) is added to 100 g. of HF and 14.4 g. 2-naphthol at −30° C. in an autoclave. The autoclave is sealed and the temperature raised to 80° C. In the manner of the first three examples, 6-hydroxy-2-acetonaphthone is prepared.

We claim:
1. A method for the acylation of a naphthalene compound of the formula:

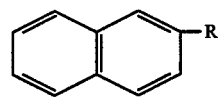

wherein R is an ortho-para directing electron-donating group not reactive with hydrogen fluoride, with an acylating agent which comprises contacting a reaction mixture of the naphthalene compound and the acylating agent with substantially anhydrous hydrogen fluoride at from about 40° to about 100° C. for a time sufficient to cause substantially complete acylation of the naphthalene compound to the 6-acylnaphthalene compound and isolating the product therefrom.

2. The method of claim 1 wherein the acylating agent is a member of the group consisting of lower alkyl carboxylic acids, lower alkyl carboxylic acid anhydrides, lower alkyl carboxylic acid halides, and ketene.

3. The method of claim 1 wherein R is a member of the group consisting of hydroxy, lower alkyl, lower alkoxy, lower alkylthio, and halo.

4. The method of claim 1 wherein the temperature of acylation is from about 60° to about 80° C. and the time of reaction is from about 30 to about 90 minutes.

5. The method of claim 1 wherein the naphthalene compound to hydrogen fluoride mole ratio in the reaction mixture is from about 1:25 to about 1:50.

6. A method for the acylation of a naphthalene compound of the formula

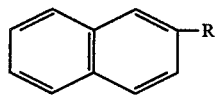

wherein R is a member of the group consisting of hydroxy, lower alkyl, lower alkoxy, lower alkylthio, and halo with an acylating agent of the group consisting of lower alkyl carboxylic acids, lower alkyl carboxylic acid anhydrides, lower alkyl carboxylic acid halides, and ketene by contacting a reaction mixture of the naphthalene compound and the acylating agent with substantially anhydrous hydrogen fluoride at from about 40 to about 100° C. for a time sufficient to cause substantially complete acylation of the naphthalene compound to the corresponding 6-acylnaphthalene compound and isolating the product therefrom.

7. The method of claim 6 wherein the temperature of acylation is from about 60° to 80° C. and the time of reaction is from about 30 minutes to about 90 minutes.

8. The method of claim 6 wherein the naphthalene compound to hydrogen fluoride mole ratio in the reaction mixture is from about 1:25 to about 1:50.

9. A method for the manufacture of 6-hydroxy-2-acetylnaphthalene which comprises contacting a reaction mixture of acetic anhydride and 2-naphthol with hydrogen fluoride in a mole ration of 2-naphthol to hydrogen fluoride of 1:50 at from about 60° to about 80° C. for about 30 minutes to about 90 minutes and isolating the product therefrom.

10. The method of claim 9 wherein the reaction is carried out at about 80° C. for about 60 minutes.

* * * * *